(12) United States Patent
Dierking

(10) Patent No.: US 9,114,000 B2
(45) Date of Patent: Aug. 25, 2015

(54) APPARATUS AND METHODS TO ENHANCE BONDING IN ENDOLUMINAL PROSTHESES

(75) Inventor: William K. Dierking, Louisville, KY (US)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 0 days.

(21) Appl. No.: 13/415,395

(22) Filed: Mar. 8, 2012

(65) Prior Publication Data

US 2012/0239134 A1    Sep. 20, 2012

Related U.S. Application Data

(60) Provisional application No. 61/452,435, filed on Mar. 14, 2011.

(51) Int. Cl.
*A61F 2/06* (2013.01)
*A61F 2/07* (2013.01)
*A61F 2/89* (2013.01)

(52) U.S. Cl.
CPC ... *A61F 2/07* (2013.01); *A61F 2/89* (2013.01); *A61F 2002/072* (2013.01); *A61F 2002/075* (2013.01); *A61F 2220/005* (2013.01); *A61F 2220/0075* (2013.01); *A61F 2250/0014* (2013.01)

(58) Field of Classification Search
CPC ............... A61F 2/86; A61F 2/89; A61F 2/82
USPC ........... 623/1.13, 1.14, 1.15, 1.42, 1.32, 1.33, 623/1.26, 1.34, 1.35, 1.51
See application file for complete search history.

(56) References Cited

U.S. PATENT DOCUMENTS

| 5,897,589 | A | * | 4/1999 | Cottenceau et al. | ......... 623/1.13 |
| 6,042,605 | A | * | 3/2000 | Martin et al. | ................ 623/1.13 |
| 6,156,064 | A | | 12/2000 | Chouinard | |
| 6,221,102 | B1 | * | 4/2001 | Baker et al. | .................. 623/1.36 |
| 6,312,458 | B1 | * | 11/2001 | Golds | ........................ 623/1.13 |
| 6,451,050 | B1 | | 9/2002 | Rudakov et al. | |
| 6,790,225 | B1 | | 9/2004 | Shannon et al. | |
| 6,939,377 | B2 | | 9/2005 | Jayaraman et al. | |

(Continued)

FOREIGN PATENT DOCUMENTS

| EP | 0686379 | 12/1995 |
| EP | 0893108 | 1/1999 |

(Continued)

OTHER PUBLICATIONS

Extended European Search Report dated Dec. 6, 2012 for EP12159478, 9 pgs.
Applicant's response to Written Opinion dated Jul. 4, 2013 for EP 12 159 478.2, 12 pgs.

(Continued)

*Primary Examiner* — Katrina Stransky
(74) *Attorney, Agent, or Firm* — Brinks Gilson & Lione

(57) ABSTRACT

The present embodiments provide an endoluminal prosthesis comprising a first membrane having a lumen for allowing fluid flow, and a stent having contracted and expanded states. At least one surface enhancement member, separate from the stent, is secured to the stent prior to a coxial overlapping state of the stent and the first membrane. The at least one surface enhancement member has stronger bonding properties with the first membrane, relative to bonding properties of bare surfaces of the stent with the first membrane, when the stent and the first membrane are in the coaxially overlapping state.

17 Claims, 10 Drawing Sheets

(56) References Cited

U.S. PATENT DOCUMENTS

| | | | |
|---|---|---|---|
| 2002/0165601 A1 | 11/2002 | Clerc | |
| 2003/0055484 A1* | 3/2003 | Lau et al. | 623/1.13 |
| 2005/0154446 A1* | 7/2005 | Phillips et al. | 623/1.13 |
| 2005/0278013 A1 | 12/2005 | Rust et al. | |
| 2007/0196420 A1 | 8/2007 | Dwyer | |
| 2008/0114446 A1* | 5/2008 | Hartley et al. | 623/1.13 |
| 2008/0319530 A1 | 12/2008 | Leewood et al. | |
| 2009/0164001 A1 | 6/2009 | Biggs et al. | |
| 2009/0211076 A1 | 8/2009 | Schlun | |
| 2009/0248131 A1 | 10/2009 | Greenan | |
| 2009/0319023 A1 | 12/2009 | Hildebrand et al. | |
| 2010/0198333 A1* | 8/2010 | Macatangay et al. | 623/1.15 |

FOREIGN PATENT DOCUMENTS

| | | |
|---|---|---|
| EP | 0997115 | 5/2000 |
| WO | WO01/52771 | 7/2001 |
| WO | WO2008/156683 | 12/2008 |

OTHER PUBLICATIONS

Examination Report dated Aug. 8, 2013 for EP 12 159 478.2, 4 pgs.
Reply to Examination Report for European Patent Application No. 12159478.2 filed Jan. 17, 2014, 5 pgs.
Examination Report No. 1 for Australian Patent Application No. 2012201505 issued Jan. 22, 2013, 4 pgs.
Reply to Examination Report No. 1 for Australian Patent Application No. 2012201505 filed Jan. 13, 2014, 5 pgs.
Examination Report No. 2 for Australian Patent Application No. 2012201505 issued Jan. 15, 2014, 5 pgs.
Examination Report dated Nov. 10, 2014 for European Patent Application No. 12 159 478.2, 6 pgs.
Response to Examination Report No. 2 for Australian Patent Application No. 2012201505 filed Mar. 19, 2014, 5 pgs.
Notice of Acceptance for Australian Patent Application No. 2012201505 dated Apr. 9, 2014, 2 pgs.
Response to Examination Report filed Mar. 9, 2015 for European Patent Application No. 12 159 478.2, 8 pgs.

* cited by examiner

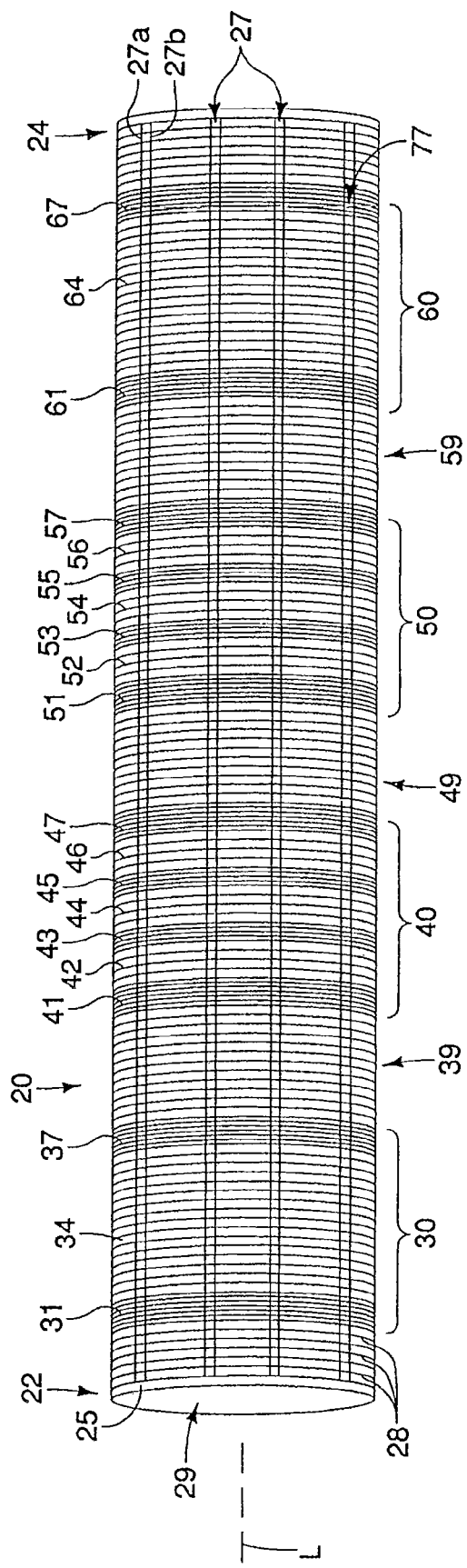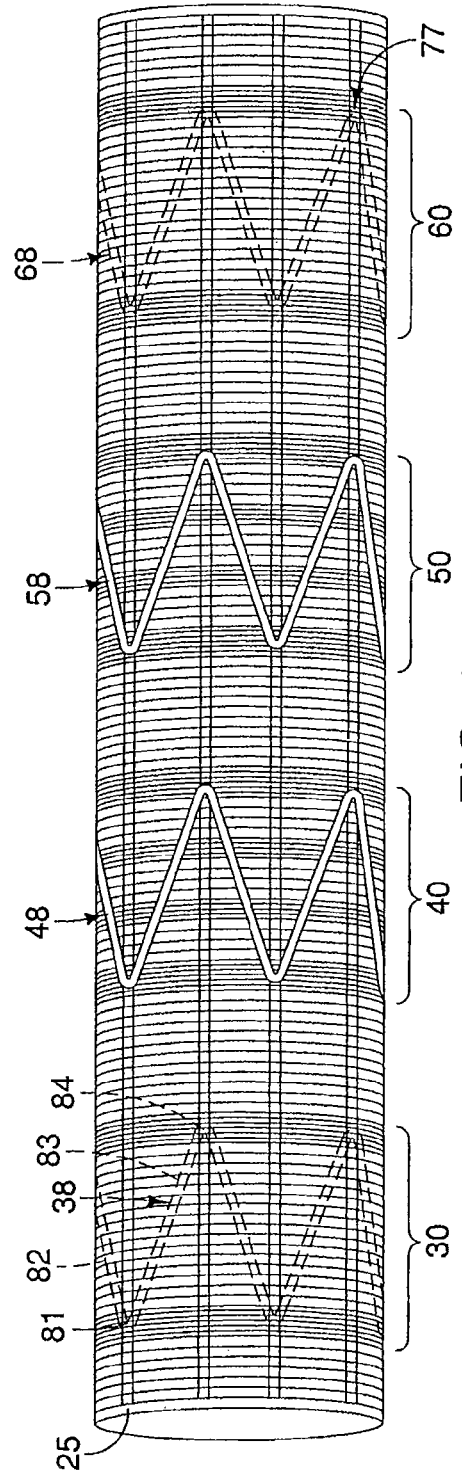

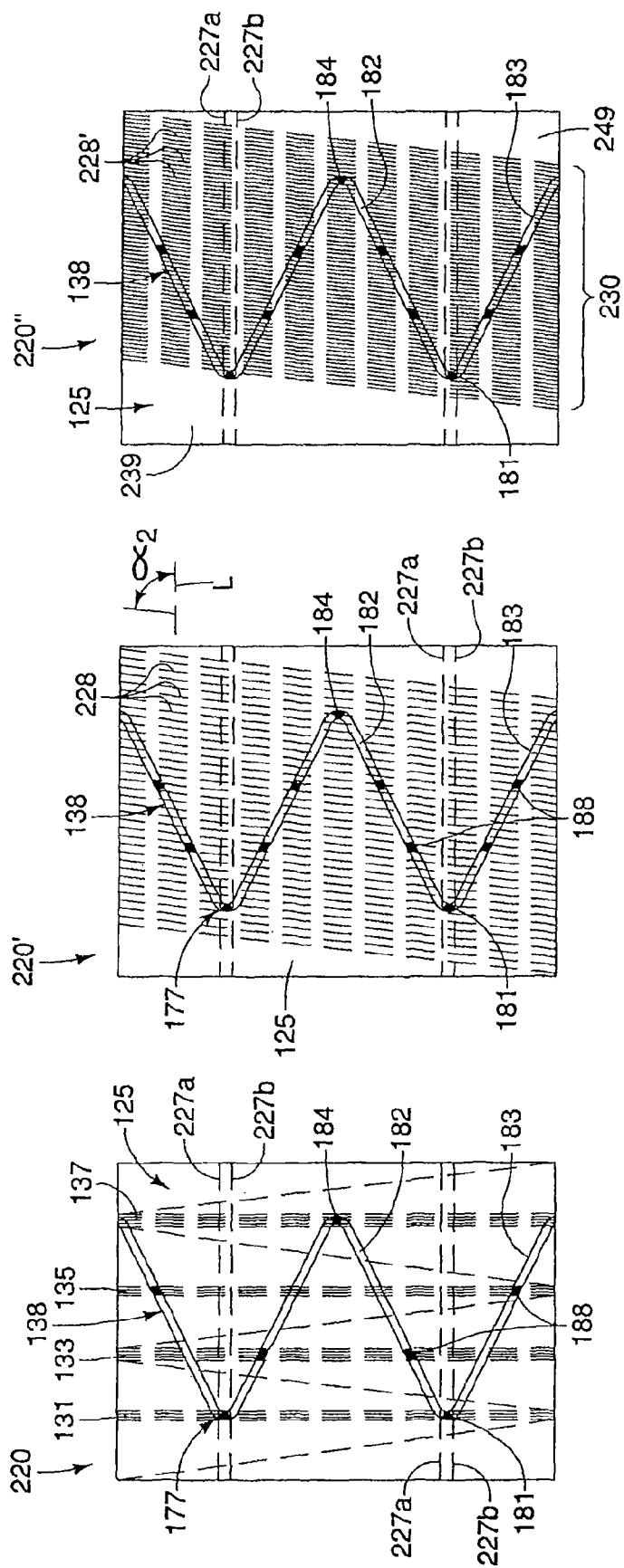

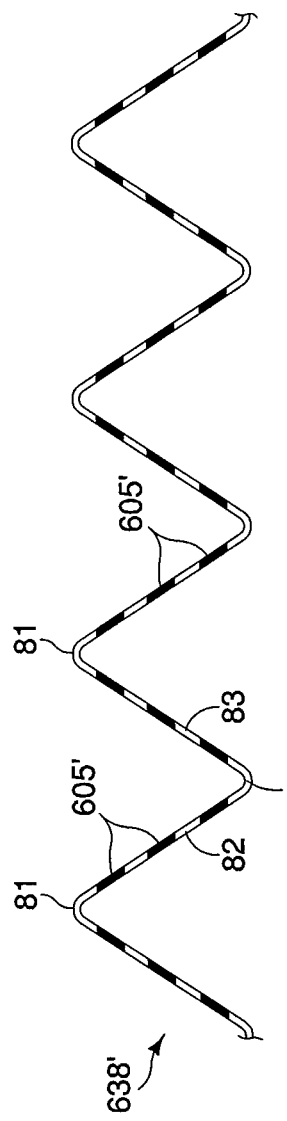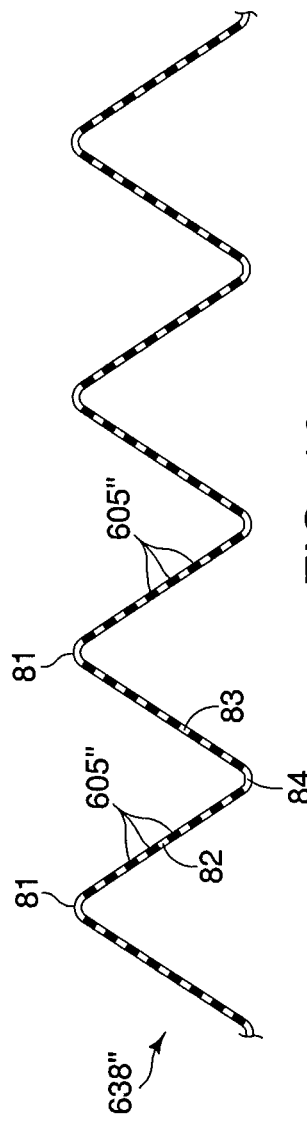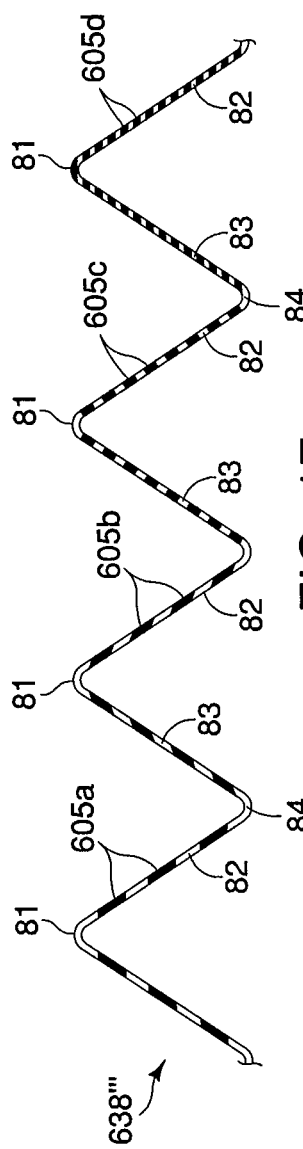

APPARATUS AND METHODS TO ENHANCE BONDING IN ENDOLUMINAL PROSTHESES

PRIORITY CLAIM

This invention claims the benefit of priority of U.S. Provisional Application Ser. No. 61/452,435, entitled "Apparatus and Methods to Enhance Bonding in Endoluminal Prostheses," filed Mar. 14, 2011, the disclosure of which is hereby incorporated by reference in its entirety.

BACKGROUND

Apparatus and methods for treating vascular conditions, and more specifically, materials for use in treating such conditions, are described.

Stent-graft assemblies may be used to treat a number of medical conditions. One common use of stent-graft assemblies relates to the treatment of an aneurysm, which is an abnormal widening or ballooning of a portion of an artery that may be caused by a weakness in the blood vessel wall. Another common use relates to the treatment of an aortic dissection, a tear in the inner wall of the aorta that causes blood to flow between the layers of the wall of the aorta and force the layers apart. If the dissection tears the aorta completely open (through all three layers), massive and rapid blood loss occurs. In many cases, the internal bleeding is so massive that a patient can die within minutes of an aneurysm or dissection rupture. For example, the survival rate after a rupture may be as low as 20%.

In an endovascular treatment of a blood vessel using a stent-graft, the stent-graft is positioned in the blood vessel across the aneurysm, e.g., using catheter-based placement techniques. The stent-graft treats the aneurysm by sealing the wall of the blood vessel with a generally impermeable graft material. Thus, the aneurysm is sealed off and blood flow is kept within the primary passageway of the blood vessel. Similarly, stent-grafts treat dissections by closing up the tear and flow is kept within the primary passageway of the blood vessel. Although stent-grafts are frequently used for treating aneurysms, other medical treatments also use stent-grafts and still other uses are possible, such as uses for stenosed arteries or other conditions.

Various types of stent-grafts are constructed with a stent disposed inside graft material, outside of graft material, or between inner and outer layers of graft material. The stents commonly are coupled to the one or more layers of graft material, by various methods.

SUMMARY

The present embodiments provide an endoluminal prosthesis comprising a first membrane having a lumen for allowing fluid flow, and a stent having contracted and expanded states. At least one surface enhancement member, separate from the stent, is secured to the stent prior to a coxial overlapping state of the stent and the first membrane. The at least one surface enhancement member has stronger bonding properties with the first membrane, relative to bonding properties of bare surfaces of the stent with the first membrane, when the stent and the first membrane are in the coaxially overlapping state.

In one embodiment, the first membrane comprises a polymer solution, and curing of the polymer solution causes surfaces of the at least one surface enhancement member to securely bond with the polymer solution. Optionally, a second membrane may be provided, where the first membrane is disposed internal to the stent, and the second membrane is disposed external to the stent.

In one example, the at least one surface enhancement member comprises a filament, such as a suture material, that is wrapped around a perimeter of at least one segment, such as a strut segment, of the stent. The at least one surface enhancement member may be wrapped around a segment of the stent in a helical manner. Optionally, the at least one surface enhancement member may be wrapped around a first segment of the stent at a first pitch and wrapped around a second segment of the stent at a second pitch, where the first and second pitches are different from one another. Further, the at least one surface enhancement member may be continuously wrapped around a length of the stent and knotted upon itself.

In one embodiment, the stent comprises a zig-zag shape having a plurality of generally straight segments separated by proximal and distal apices. In this example, the at least one surface enhancement member may be wrapped around at least a portion of each of the generally straight segments and the proximal and distal apices.

The endoluminal prosthesis may further comprise a plurality of circumferential fibers arranged in a desired orientation relative to the first membrane, where the first membrane bonds with the at least one surface enhancement member and the plurality of circumferential fibers. Optionally, a plurality of axial fibers also may be provided, where the first membrane bonds with the at least one surface enhancement member, the plurality of circumferential fibers, and the plurality of axial fibers.

Advantageously, the completed prosthesis yields an enhanced structural integrity without the need for coupling the stent to the first membrane using conventional suturing techniques, which may be time-consuming. Test data shows that prostheses employing the at least one surface enhancement member secured to the stent significantly enhances the bond of the membrane and the surface enhancement member, relative to the bond between membranes and stents that omitted the at least one surface enhancement member. In particular, a cured membrane better adheres to the surfaces of the at least one surface enhancement member secured to the stent, as opposed to the bare metal surfaces of the stent.

Other systems, methods, features and advantages of the invention will be, or will become, apparent to one with skill in the art upon examination of the following figures and detailed description. It is intended that all such additional systems, methods, features and advantages be within the scope of the invention, and be encompassed by the following claims.

BRIEF DESCRIPTION OF THE DRAWINGS

The invention can be better understood with reference to the following drawings and description. The components in the figures are not necessarily to scale, emphasis instead being placed upon illustrating the principles of the invention. Moreover, in the figures, like referenced numerals designate corresponding parts throughout the different views.

FIG. 1 is side view of a stent-graft according to a first embodiment with stents removed for illustrative purposes.

FIG. 2 is side view of the stent-graft of FIG. 1 with stents shown.

FIGS. 5-7 are side views of portions of various stent-grafts provided in accordance with further alternative embodiments.

FIGS. 15-17 are schematic views illustrating alternative arrangements of a stent and at least one surface enhancement member.

DETAILED DESCRIPTION OF THE PREFERRED EMBODIMENTS

Figure 4:
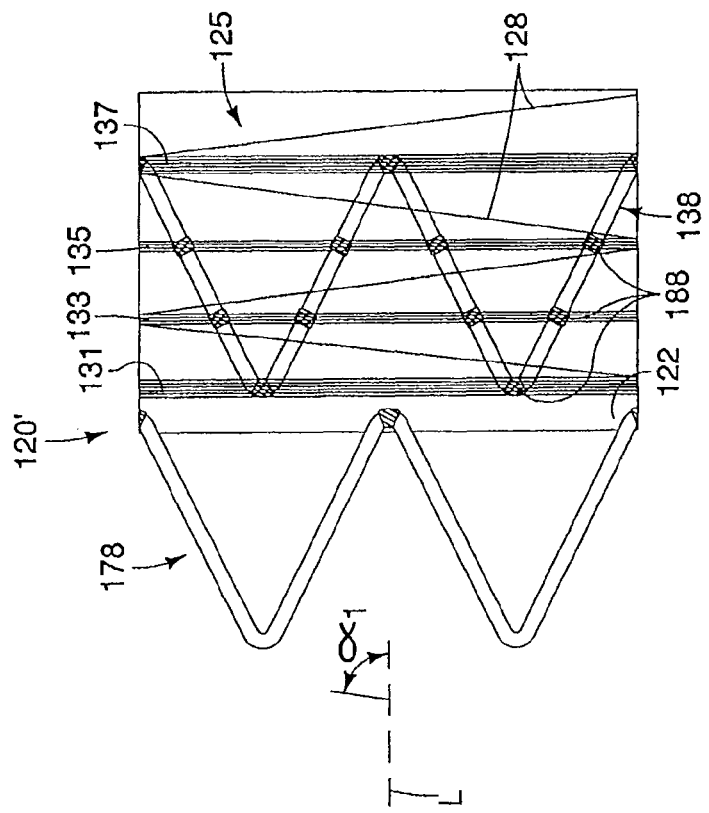
FIG. 4 is a side view of a proximal portion of a stent-graft provided in accordance with a further alternative embodiment.

In the present application, the term "proximal" refers to a direction that is generally closest to the heart during a medical procedure, while the term "distal" refers to a direction that is furthest from the heart during a medical procedure.

Referring now to FIGS. 1-2, a first embodiment of a stent-graft 20 is shown. As shown in FIG. 1, the stent-graft 20 comprises a membrane 25 having proximal and distal ends 22 and 24, respectively, and a lumen 29 extending therebetween that is dimensioned for fluid flow for a given application.

The stent-graft 20 further comprises at least one axial fiber 27 and at least one circumferential fiber 28. Preferably, a plurality of axial fibers 27 and circumferential fibers 28 are provided, and are arranged in predetermined patterns for one or more desired functions, such as providing stent attachment locations and/or being positioned in regions along the stent-graft 20 that are subject to relatively high hydrodynamic forces, as explained further below. For example, the axial fibers 27 may assist in withstanding longitudinally-oriented blood flow forces, while the circumferential fibers 28 may assist in withstanding pulsatile flow forces.

Advantageously, by selectively orienting the axial fibers 27 and circumferential fibers 28 at predetermined locations along the length and circumference of the stent-graft 20, but not continuously along the entire stent-graft, a significantly reduced delivery profile may be achieved due to the reduction in fiber material.

In the exemplary embodiment of FIGS. 1-2, the stent-graft 20 comprises a plurality of distinct regions, each for accommodating a stent or portion of a stent. By way of example, four distinct regions 30, 40, 50 and 60 are provided for accommodating stents 38, 48, 58 and 68, respectively. Each of the four distinct regions 30, 40, 50 and 60 comprises a predetermined arrangement of axial fibers 27 and circumferential fibers 28 for accommodating the respective stents 38, 48, 58 and 68.

For example, the first distinct region 30 may be disposed near the proximal end 22 of the prosthesis. As shown in FIG. 1, the first distinct region 30 comprises a plurality of circumferential fibers 28 arranged in predetermined orientations. In particular, a proximal bundled region 31 of the first distinct region 30 comprises multiple circumferential fibers 28 coupled to the membrane 25. The circumferential fibers 28 are arranged such that at least two adjacent circumferential fibers 28 within the proximal bundle 31 are separated by a first spacing.

The first distinct region 30 further comprises a distal bundled region 37 that, like the proximal bundled region 31, comprises at least two adjacent circumferential fibers 28 separated by the same first spacing as the proximal bundled region 31. The proximal and distal bundled regions 31 and 37 may comprise a desired number of circumferential threads per inch ("TPI").

The first distinct region 30 further comprises at least one non-bundled region 34, which is disposed between the proximal and distal bundled regions 31 and 37. The non-bundled region 34 comprises at least two adjacent circumferential fibers 28 that are separated by a second spacing, which is greater than the first spacing. In other words, as depicted in FIGS. 1-2, at least some, if not all, of the circumferential fibers 28 of the non-bundled region 34 are separated by a greater spacing as compared to the circumferential fibers 28 of the proximal and distal bundled regions 31 and 37. Notably, in one embodiment, the first spacing may be zero, i.e., there is no separation of fibers.

In the example of FIGS. 1-2, the proximal and distal bundles 31 and 37 may have a greater TPI count of circumferential fibers 28 relative to the non-bundled region 34. Solely by way of example, and without limitation, the proximal and distal bundled regions 31 and 37 may have a thread count between about 20 to about 120 TPI. In contrast, the non-bundled region 34 may have a thread count of less than 20 TPI. Therefore, in this example, there is a non-uniform circumferential fiber population density along at least a portion of the stent-graft 20. Additionally, the number of fibers in each of the bundled and non-bundled regions may also vary. For example, one bundled region may have more fibers than another bundled region, and similarly for the non-bundled regions.

In one example, the first spacing within the proximal and distal bundled regions 31 and 37 may be such that the spacing between individual circumferential fibers 28 is less than or equal to the width of the fibers themselves. Thus, adjacent circumferential fibers may abut one another directly, or may be separated but disposed in such close proximity such that another fiber of the same width cannot be disposed therebetween without overlap. By contrast, circumferential fibers 28 disposed in the non-bundled region 34 are not in direct proximity to one another, such that the second spacing between individual circumferential fibers 28 is greater than the width of the fibers themselves. The spacing between the fibers in each of the bundled regions need not be identical. Similarly, the spacing of the fibers in the non-bundled regions need not be identical.

Figure 8:
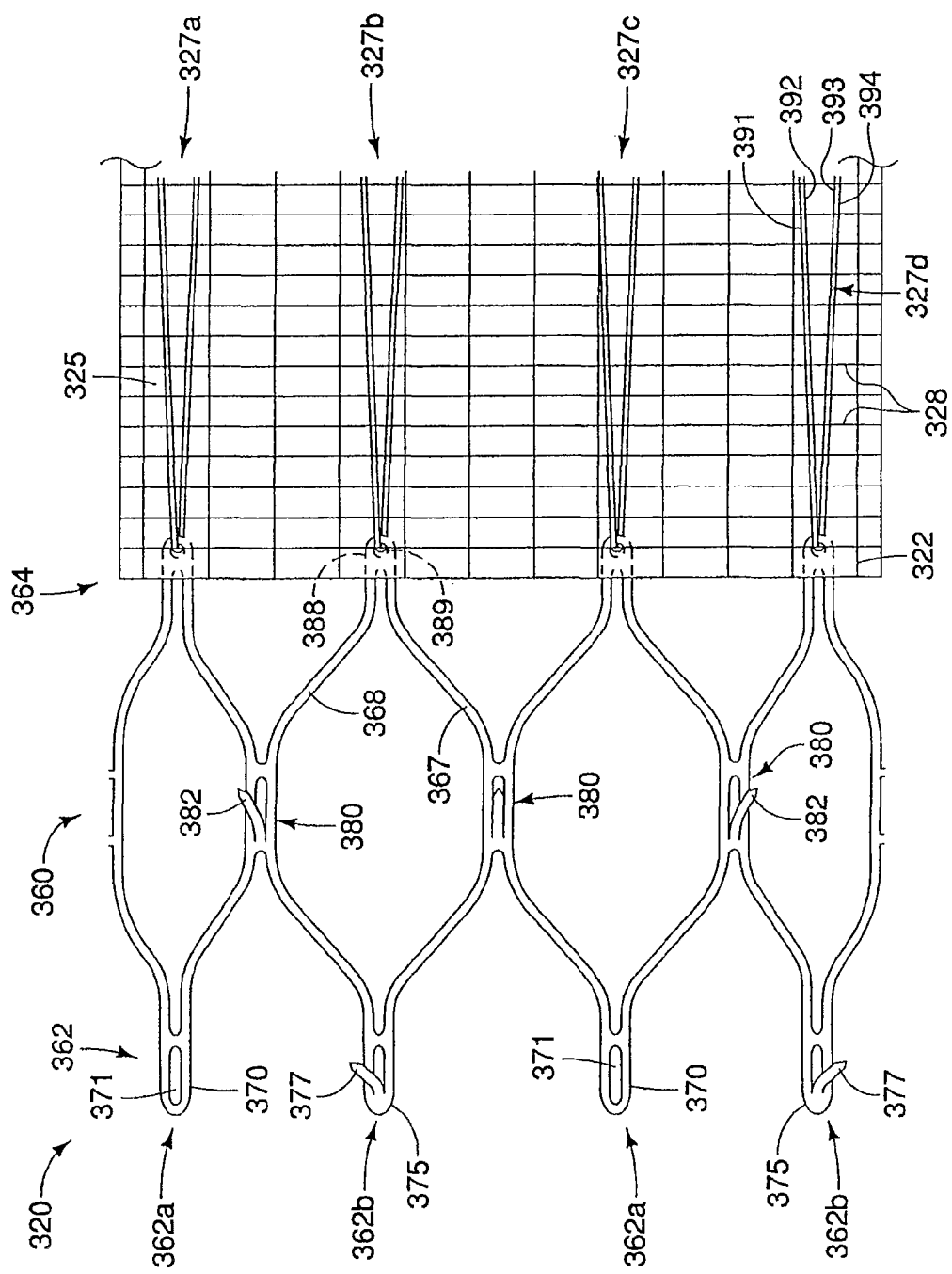
FIG. 8 is a side view of a proximal portion of a stent-graft provided in accordance with a further alternative embodiment.

The stents 38, 48, 58 and 68 may comprise any suitable shape for providing desired support to the stent-graft 20. In one non-limiting example, shown herein, the stents may comprise a generally zig-zag shape formed from a single wire comprising a plurality of substantially straight first segments 82 and second segments 83 having bent segments disposed therebetween, the bent segments in the form of proximal apices 81 and distal apices 84. In one embodiment, each of the proximal apices 81 of the first stent 38 is positioned to overlap with the proximal bundled region 31, and each of the distal apices 84 of the first stent 38 is positioned to overlap with the distal bundled region 37, as shown in FIG. 2. While z-stents are depicted herein, the embodiments are not limited to z-stents and other stent structures may be used. For example, the stent structure shown in FIG. 8 is another non-limiting example of a suitable stent.

By selectively overlapping the proximal apices 81 of the first stent 38 with the proximal bundled region 31, an enhanced suture attachment site may be provided due to the close proximity of the circumferential sutures 28 within the proximal bundle 31. For example, it may be easier to suture the proximal apices 81 of the stent 38 to the stent-graft 20 in areas where circumferential fibers are bundled, instead of relatively spaced apart or lacking entirely. Similarly, by selectively overlapping the distal apices 84 of the first stent 38 with the distal bundled region 37, an enhanced suture attachment site may be provided due within the distal bundled region 37.

Moreover, in the example of FIGS. 1-2, at least two axial fibers 27a and 27b preferably overlap with the various circumferential fiber bundles at intersections 77. Each of the proximal and distal apices 81 and 84 of the stent 38 may be aligned with one of the intersections 77, as shown in FIG. 2. Thus, each of the proximal and distal apices 81 and 84 of the stent 38 may be secured to the stent-graft 20 in regions where a circumferential fiber bundled region meets axial fibers 27, thereby providing selective suture attachment zones for the stent 38. Notably in this example, there is a selective axial fiber density along at least a portion of the stent-graft 20, since axial fibers 27 are intended to only line up with the proximal and distal apices of a given stent and the fibers.

As a further advantage, by selectively orienting axial fibers 27 and circumferential fibers 28 at predetermined locations along the length and circumference of the stent-graft 20, e.g., at specific points of attachment of proximal and distal stent apices, but not continuously along the entire stent-graft 20, a significantly reduced delivery profile may be achieved due to the reduced presence of fiber material.

Referring still to FIGS. 1-2, in this embodiment the other stents 48, 58 and 68 may be attached to the stent-graft 20 in a similar manner. In particular, the stent 48 may be positioned to overlap with the second distinct region 40. The second distinct region 40 may comprise a proximal bundled region 41, intermediate bundled regions 43 and 45, and a distal bundled region 47, each comprising at least some circumferential fibers 28 disposed with the first spacing relative to one another, as shown in FIG. 1. Non-bundled regions 42, 44 and 46 may be disposed between the various bundled regions 41, 43, 45 and 47, as shown in FIG. 1. Like the stent 30, each of the proximal and distal apices 81 and 84 of the stent 48 may be secured to the stent-graft 20 at intersections 77 where a circumferential fiber bundle meets axial fibers 27. Specifically, the proximal apices 81 of the stent 48 are attached to the stent-graft 20 where proximal bundled region 41 meets axial fibers 27, while the distal apices 84 of the stent 48 are attached to the stent-graft 20 where distal bundled region 47 meets axial fibers 27. Further, the stent 48 may be secured to the stent-graft 20 at locations in which the substantially straight first segments 82 and second segments 83 of the stent 48 overlap with the intermediate bundles 43 and 45. In this manner, multiple specific suture attachment zones are provided for the stent 48 at the bundled regions 41, 43, 45 and 47, while the provision of non-bundled regions 42, 44 and 46 may contribute to reducing the overall profile of the stent-graft 20 while preferably comprising some circumferential fibers for distributing loads.

Stent 58 may be positioned to overlap with the third distinct region 50 in a similar manner that stent 48 is positioned relative to the second distinct region 40. Specifically, the third distinct region 50 may comprise a proximal bundled region 51, intermediate bundled regions 53 and 55, and a distal bundled region 57, while non-bundled regions 52, 54 and 56 are disposed between the various bundles regions 51, 53, 55 and 57. Like the stents 30 and 40, each of the proximal and distal apices 81 and 84 of the stent 58 may be secured to the stent-graft 20 at intersections 77 where a circumferential fiber bundle meets axial fibers 27.

Finally, stent 68 may be positioned to overlap with the fourth distinct region 60 in a similar manner that stent 38 is positioned relative to the first distinct region 30. Specifically, the fourth distinct region 60 comprise proximal and distal bundled regions 61 and 67, with non-bundled region 64 disposed therebetween. Like the stent 30, each of the proximal and distal apices 81 and 84 of the stent 68 may be secured to the stent-graft 20 at intersections 77 where a circumferential fiber bundle meets axial fibers 27.

Notably, non-bundled spacing regions 39, 49 and 59 are positioned between the distinct regions 30, 40, 50 and 60, as shown in FIGS. 1-2. Circumferential fibers of the non-bundled spacing regions 39, 49 and 59 may comprise the second spacing relative to one another, i.e., a greater spacing than in the bundled regions. Thus, there is a reduction in fiber material in the non-bundled spacing regions 39, 49 and 59, contributing to a reduced delivery profile.

Beneficially, a fiber-reinforced polymer matrix may be provided that is designed to carry the necessary supporting stents, plus withstand known loading conditions during long term use in a particular application, such as in endovascular use.

While intermediate bundled regions are shown only for the second and third distinct regions 40 and 50, it will be apparent that any of the various distinct regions 30, 40, 50 and 60 may comprise one or more intermediate bundled regions, or the various distinct regions each may omit intermediate bundled regions. Moreover, the exact placement of the bundled and non-bundled regions may be varied, e.g., based on desired stent attachment sites, hydrodynamic forces expected to be imposed upon on the stent-graft 20, and other factors.

The membrane 25 may be disposed internal or external to the axial fibers 27 and circumferential fibers 28. In the example of FIGS. 1-2, the membrane 25 is disposed internal to both the axial and circumferential fibers 27 and 28, but this is not required. In this instance, the membrane 25 may be formed upon a mandrel, with the desired circumferential and axial fiber pattern being deposited externally thereof.

Further, the stents 38, 48, 58 and 68 may be positioned external and/or internal relative to the membrane 25, as well as external and/or internal relative to the axial fibers 27 and circumferential fibers 28. In the example of FIGS. 1-2, the stents 38 and 68 are disposed internal (dashed lines) relative to the membrane 25, while the stents 48 and 58 are disposed external of both the membrane 25 and the axial and circumferential fibers 27 and 28. However, various combinations of internal and external positioning of the membrane, stents and fibers are possible. Moreover, lamination and/or embedding of the stents between two membranes may be provided in lieu of suturing the stents. In the latter embodiment, selective fiber densities still may be provided for the purpose of providing reinforcement areas for expected physiological forces.

During manufacture, the materials may be placed on a mandrel in a desired orientation. In one exemplary manufacturing step, the stent-graft 20 may be prepared by mounting the membrane 25 on a mandrel and then overlaying the axial fibers 27 and circumferential fibers 28 in a desired orientation. Alternatively, the axial fibers 27 and circumferential fibers 28 may be arranged on the mandrel in a desired orientation, then the membrane 25 may be disposed over the fibers. In one other embodiment, the axial fibers 27 and circumferential fibers 28 may be arranged on the mandrel in a desired orientation, then the stents 38, 48, 58 and 68 may be laid over the fibers, and then the membrane 25 may be disposed over the fibers and the stents. As a further alternative, one membrane may be placed on the mandrel, then the axial fibers 27 and circumferential fibers 28 may be deposited onto the first mandrel, and then a second membrane may be deposited over the first membrane and the axial and circumferential fibers 27 and 28. Still further, only some fibers may be applied to the mandrel, such as the circumferential fibers 28, then the membrane 25 may be deposited thereon, and then other fibers, such as the axial fibers 27, may be deposited over the circumferential fibers 28 and the membrane 25. In sum, various assembly combinations are possible.

Various mechanisms may be used to correctly deposit and align the axial fibers 27 and circumferential fibers 28 in the desired orientation, such as automated CNC deposition. The membrane 25 with axial and circumferential fibers 27 and 28 then may be mounted on a lathe. The lathe may be rotated at a proper speed, such as 20 rpm, while applying a dilute polyurethane solution to cover all of the fibers. The stent-graft 20 then may be cured or dried at about 65 degrees Celsius for about 2 hours while the lathe is rotated at the desired speed.

The stents then may be secured to the membrane 25, preferably near one or more intersections 77, as explained above. In one example, the mandrel used to assemble the materials may comprise pins at predetermined locations. Various fibers may be arranged around the pins, such that when the assembled device is removed from the mandrel, the pins have created bores. The bores created by the mandrel pins may advantageously provide a predetermined suture attachment site for subsequent attachment of the stents to the membrane.

Optionally, the stents may be coupled to the membrane 25 using polymer encapsulation as the adhesion technique, thereby eliminating the need for sutures. Regardless of the technique used to couple the stents to the membrane 25, by selectively orienting axial fibers 27 and circumferential fibers 28 at predetermined locations along the length and circumference of the stent-graft 20, but not continuously along the entire stent-graft 20, a significantly reduced delivery profile may be achieved.

In one embodiment, the membrane 25 may comprise a polymeric sheet having a suitable porosity, depending on the application. In one example, a polymeric sheet may comprise the polyurethane Thoralon®. As described in U.S. Pat. No. 6,939,377, incorporated herein by reference in its entirety, Thoralon® is a polyetherurethane urea blended with a siloxane-containing surface modifying additive. Specifically, the polymer is a mixture of base polymer BPS-215 and an additive SMA-300. The concentration of additive may be in the range of 0.5% to 5% by weight of the base polymer. The BPS-215 component (Thoratec® Corporation, Pleasanton, Calif.) is a segmented polyether urethane urea containing a soft segment and a hard segment. The soft segment is made of polytetramethylene oxide (PTMO), and the hard segment is made from the reaction of 4,4'-diphenylmethane diisocyanate (MDI) and ethylene diamine (ED). The SMA-300 component (Thoratec® Corporation, Pleasanton, Calif.) is a polyurethane comprising polydimethylsiloxane as a soft segment and the reaction product of MDI and 1,4-butanediol as a hard segment. A porous polymeric sheet can be formed from these two components by dissolving the base polymer and additive in a solvent such as dimethylacetamide (DMAC) and solidifying the mixture by solvent casting or by coagulation in a liquid that is a non-solvent for the base polymer and additive.

Thoralon® has been used in certain vascular applications and is characterized by thromboresistance, high tensile strength, low water absorption, low critical surface tension, and good flex life. Thoralon® is believed to be biostable and to be useful in vivo in long term blood contacting applications requiring biostability and leak resistance. Because of its flexibility, Thoralon® may be useful in larger vessels, such as the abdominal aorta, where elasticity and compliance are beneficial.

Further, Thoralone® may also be used as a drug delivery vehicle, for example, to deliver one or more therapeutic agents. The therapeutic agents may be coated onto or contained within a porous outer layer of the membrane 25 for sustained release subsequent to an implantation procedure and may be used, for example, to promote intimal cell ingrowth.

While Thoralon® is one example, the membrane 25 may comprise other materials. In addition to, or in lieu of, a polyurethane such as Thoralon®, the membrane 25 may comprise any biocompatible polymeric material including non-porous or substantially non-porous polyurethanes, PTFE, expanded PTFE (ePTFE), polyethylene tetraphthalate (PET), aliphatic polyoxaesters, polylactides, polycaprolactones, hydrogels, and other non-polymeric materials.

The stent-graft 20 may be used in a wide range of procedures, for example, to treat an aneurysm, stenosis, dissection or other condition. As known in the art, stents 38, 48, 58 and 68 have compressed, reduced diameter delivery states in which the stent-graft 20 may be advanced to a target location within a vessel, duct or other anatomical site, and further have expanded states, as shown in FIG. 2, in which they may be configured to apply a radially outward force upon the vessel, duct or other target location, e.g., to maintain patency within a passageway, while the lumen 29 is suitable for carrying fluid though the stent-graft 20. The stent-graft 20 may be designed specifically for treating abdominal or thoracic aneurysms or dissections. Moreover, while a single lumen device is shown, the principles used herein may be used in connection with bifurcated stent-grafts.

The stents 38, 48, 58 and 68 may be made from numerous metals and alloys. In one example, the stents 38, 48, 58 and 68 comprise a shape-memory material such as a nickel-titanium alloy ("nitinol"). Moreover, while generally zig-zag shaped stents are shown, the structure of the stents 38, 48, 58 and 68 may be formed in a variety of ways to provide a suitable intraluminal support structure. For example, one or more stents 30 may be made from a woven wire structure, a laser-cut cannula, individual interconnected rings, or another pattern or design. Depending on the stent structure employed, the position of the fiber bundles may be varied to provide appropriate suture attachment sites in a manner similar to the zig-zag stent example of FIGS. 1-2.

Figure 3:
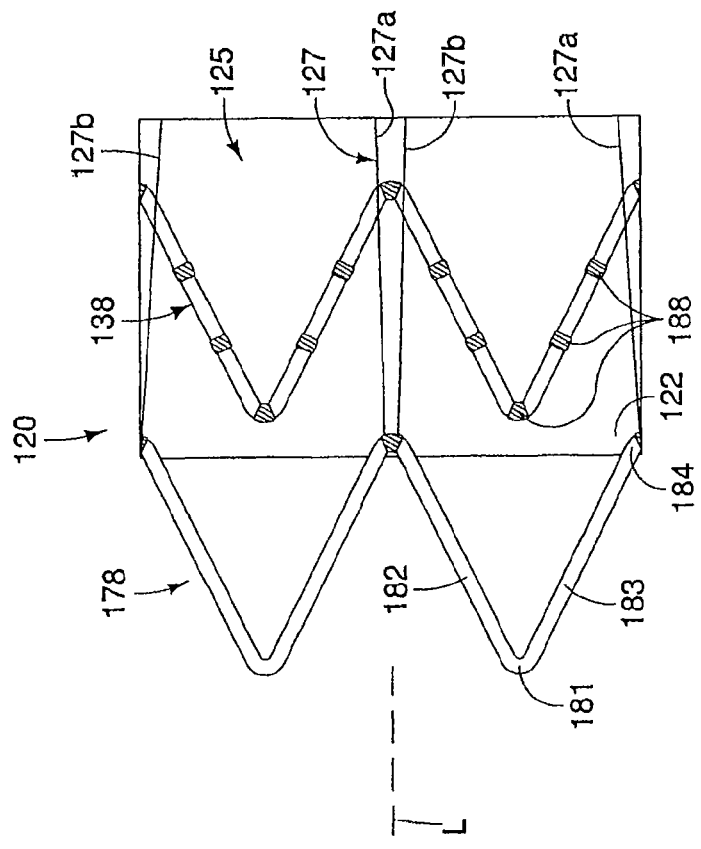
FIG. 3 is a side view of a proximal portion of a stent-graft provided in accordance with an alternative embodiment.

Referring now to FIGS. 3-8, various alternative arrangements of components, in accordance with principles above, are shown and described. For example, in FIG. 3, an alternative stent-graft 120 comprises a membrane 125, stents 138 and 178, and a plurality of angled axial fibers 127. The membrane 125 is similar to the membrane 25 of FIGS. 1-2, and the stents 138 and 178 are similar to the stent 38 of FIGS. 1-2. In this example, the stent 178 is affixed to the proximal end 122 of the membrane 125 and has first and second substantially straight segments 182 and 183 separated by proximal and distal apices 181 and 184. Each of the distal apices 184 may be connected to the proximal end 122 of the membrane 125, as shown in FIG. 3. Furthermore, the stent 138 is coupled to the membrane 125 using a plurality of sutures 188 or other attachment methods as discussed. A plurality of circumferential fiber bundled regions 131, 133, 135 and 137, shown in FIG. 4, may be used in the embodiment of FIG. 3 to provide attachment zones for the sutures 188 to the membrane 125 in the manner noted above in FIGS. 1-2.

In this example, each of the angled axial fibers 127 are disposed around one of the distal apices 184 of the stent 178. The angled axial fibers 127 therefore each form first and second segments 127a and 127b that extend in a distal direction away from the stent 178. The first and second segments 127a and 127b of the angled axial fibers 127 may extend at an angle relative to a longitudinal axis L of the stent-graft. For example, the angle may range from about 1 to about 15 degrees, as depicted in FIG. 3. Notably, such angled axial fibers segments 127a and 127b may be more compliant than the axial and circumferential fibers 27 and 28 shown above, thereby selectively providing compliant support at predetermined locations.

Referring now to FIG. 4, an exemplary alternative stent-graft 120' is similar to stent-graft 120, and comprises a membrane 125 and stents 138 and 178. A plurality of axial fibers, such as angled axial fibers 127 of FIG. 3, may be employed but are omitted in the illustration. In this example, a plurality of circumferential fibers 128 is provided. Unlike the circumferential sutures 28 of FIGS. 1-2, which are generally perpendicular to the longitudinal axis L of the stent-graft, the circumferential fibers 128 are disposed at angle $\alpha_1$ relative to the longitudinal axis L of the stent-graft, as shown in FIG. 4. In one example, the angle $\alpha_1$ may range from about 70 to about 89 degrees. Like the angled axial fibers segments 127a and 127b of FIG. 3, the angled circumferential fibers 128 of FIG. 4 may be more compliant than the circumferential fibers 28, thereby selectively providing compliant support at predetermined locations.

Referring now to FIGS. 5-7, various alternative stent-grafts are shown. Notably, in FIGS. 5-7, various circumferential, axial and angled fibers are depicted with dashed lines for illustrative purposes only, but it is preferred that such circumferential, axial and angled fibers are generally formed from continuous filaments. In FIG. 5, an alternative stent-graft is similar to stent-graft 120, with like reference numerals labeled accordingly. In FIG. 5, at least two axial fibers 227a and 227b preferably overlap with the various circumferential fiber bundled regions 131, 133, 135 and 137 at intersections 177. Each of the proximal apices 181 of the stent 138 may be aligned with one of the intersections 177, as shown in FIG. 5. Thus, each of the proximal apices 181 of the stent 138 may be secured to the stent-graft 220 in regions where a circumferential fiber bundle meets axial fibers 227a and 227b, thereby permitting a significantly enhanced suture attachment zone for at least the proximal apices 181 of the stent 38. Optionally, additional axial fibers may be provided that coincide with the distal apices 184 in a similar manner.

Referring now to FIG. 6, an alternative stent-graft 220' is similar to the stent-graft 220 of FIG. 5. However, in FIG. 6, the plurality of circumferential bundled regions 131, 133, 135 and 137 are omitted, and a plurality of angled circumferential fibers 228 are utilized. The angled circumferential fibers 228 are parallel to one another, but are disposed at an angle $\alpha_2$ relative to the longitudinal axis L of the stent-graft 220'. In one example, the angle $\alpha_2$ is between about 70 to about 89 degrees. Moreover, in this example, the angled circumferential fibers 228 may be wound at between about 10 to about 30 threads per inch (TPI). In FIG. 6, sutures 188 may be coupled to the membrane 125 along multiple parts of each segment 182 and 183 of the stent 138, as well as at each of the proximal and distal apices 181 and 184.

Referring now to FIG. 7, an alternative stent-graft 220" is substantially identical to the stent-graft 220' of FIG. 6. However, in FIG. 7, angled circumferential fibers 228' may be wound at between about 30 to about 50 threads per inch (TPI). Therefore, the closer bundling of angled circumferential fibers 228" in FIG. 7 may provide an enhanced site for attaching sutures 188 to the membrane 125.

Notably, in FIGS. 6-7, the angled circumferential fibers 228 are bundled together along a distinct region 230, which generally overlaps with the stent 138. Non-bundled regions 239 and 249 may exist proximal and distal to the distinct region 230, i.e., in regions where a stent is not present.

Referring now to FIG. 8, a proximal portion of an alternative stent-graft 320 is shown and described. In this example, the stent-graft 320 comprises a bare proximal stent 360 that is coupled to a membrane 325. The stent 360 may be manufactured from a continuous cylinder into which a pattern may be cut by a laser or by chemical etching to produce slits in the wall of the cylinder. The resulting structure may then be heat set to give it a desired final configuration. As shown in FIG. 8, the configuration may include a shape having a series of proximal apices and a series of distal apices. A proximal end 362 of the stent 360 may comprise multiple adjacent proximal apices 362a and 362b, while a distal end 364 of the may comprise multiple adjacent distal apices 388 having bores 389 formed therein, as shown in FIG. 8. In FIG. 4, a first proximal apex 362a may comprise an end region 370 having a bore 371 formed therein. A second, adjacent proximal apex 362b may comprise an end region 375 having an integral barb 377 formed therein. Alternatively, both proximal apices 362a and 362b may comprise integral barbs 377.

The stent 360 may comprise multiple angled strut segments disposed between a proximal apex 362a or 362b, and a corresponding distal apex 364a. By way of example, first and second angled strut segments 367 and 368 may be provided. A first angled strut segments 367 may meet with an adjacent second angled strut segment 368, thereby forming a transition region 380. Expansion of the stent 360 is at least partly provided by the angled strut segments 367 and 368, which may be substantially parallel to one another in a compressed state, but may tend to bow outward away from one another in the expanded state shown in FIG. 8. Each transition region 380 may comprise a larger surface area relative to the angled segments, and at least one barb 382 may be disposed in at least one of the transition regions 380.

Each of the distal apices 388 of the stent 380 may be coupled to a proximal end 322 of the membrane 325, for example, using one or more sutures that are looped through the graft membrane 325 and the bores 389 of the stent 360. In this manner, the stent 360 may be used as an attachment stent for endovascular graft fixation. For example, the membrane 325 may overlap with an aneurysm to seal off fluid flow into the aneurysm, while the proximal end 362 of the stent 360 may extend in a proximal direction away from the graft material, e.g., to engage a healthy portion of a vessel wall away from a diseased portion of the aneurysm. As will be apparent, one or more additional stents may be coupled to an inner or outer surface of the membrane 325, i.e., at a location distal to the stent 360, to help maintain patency throughout the graft material.

In FIG. 8, a plurality of axial fibers 327 and circumferential fibers 328 are provided, either inside or outside of the membrane 325. The plurality of axial fibers 327 and circumferential fibers 328 may be provided in accordance with the plurality of axial fibers 27 and the plurality of circumferential fibers 28, as shown in FIGS. 1-2 above.

Further, in FIG. 8, a plurality of angled axial fiber bundles 327a-327d are shown positioned external to the membrane 325, though additional angled fiber bundles that are not depicted extend around the full circumference of the membrane 325. Each of the angled axial fiber bundles 327a-327d comprises multiple segments 391-394, though greater or fewer segments may be employed. Two individual fibers within each bundle 327a-327d may be looped through the bore 389 at a distal apex 388 of the stent 360, and therefore, the two individual fibers extend distally away from the stent 360 forming the four segments 391-394. The four segments 391-394 may fan outward relative to one another, i.e., become further spaced apart relative to each other as they extend in a proximal to distal direction, as shown in FIG. 8.

It is believed that by providing axial fiber bundles 327a-327d coupled to, and extending distally from, the stent 360 in the manner shown, wherein multiple segments 391-394 fan outward relative to one another, the fibers may be oriented in a manner that reinforces strength characteristics of stent-graft 320 while maintaining its lower profile. In particular, it is believed that such a structure of FIG. 8 may selectively reinforce the membrane 325 and allow the stent-graft 320 to withstand physiological fluid flow in a proximal to distal direction.

Figure 9A:
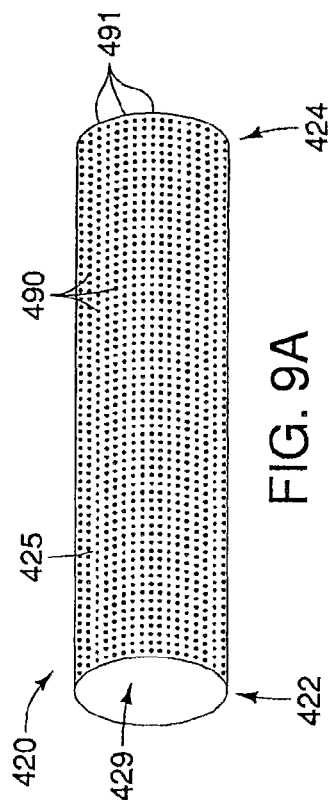
FIGS. 9A-9C illustrative exemplary methods steps for manufacturing a further alternative stent-graft.
Figure 9B:
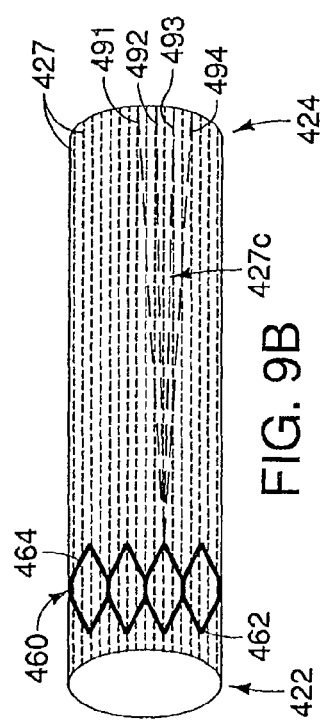
Figure 9C:
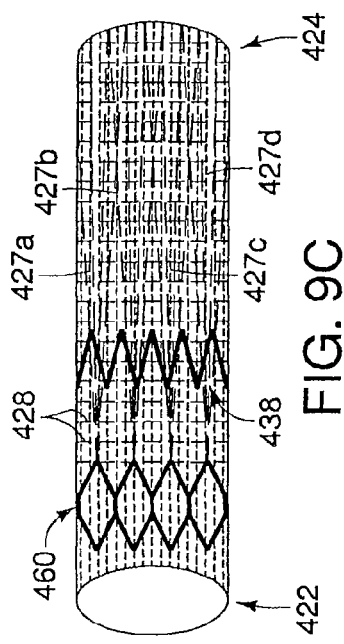

Referring now to FIGS. 9A-9C, an alternative stent-graft 420 borrows various principles from the above-described stent-grafts, and comprises a membrane 425 having proximal and distal ends 422 and 424 and a lumen 429 extending therebetween. In one optional method step, depicted in FIG. 9A, multiple holes 490 may be drilled around the circumference of the membrane 425, thereby forming a plurality of rows 491. In one embodiment, about forty rows 491 may be formed. Then, a corresponding number of axial fibers 427 may be coupled to the membrane 425, as shown in FIG. 9B. For example, each axial fiber 427 may be looped through the holes 490 of a particular row 491. Alternatively, the holes 490 may be omitted and a desired number of axial fibers 427 may be arranged internal or external to or within the membrane 425.

In FIG. 9B, after the axial fibers 427 have been coupled to the membrane 425, a proximal attachment stent 460 may be disposed external to the axial fibers 427. The stent 460 may be similar to the stent 360 described in FIG. 8, and may comprises a plurality of proximal and distal apices 462 and 464. A plurality of angled axial fiber bundles 427a-427d may be coupled to the stent 460 external to the membrane 425, as shown in FIGS. 9B-9C. Each of the angled axial fiber bundles 427a-427d comprises multiple segments 491-494, though greater or fewer segments may be employed. Two individual fibers within each bundle 427a-427d may be looped through bores at a distal apex 464 of the stent 460, in the manner shown in FIG. 8 above, and therefore the two individual fibers extend distally away from the stent 460 forming the four segments 491-494. The four segments 491-494 may fan outward relative to one another, i.e., become further spaced apart relative to each other as they extend in a proximal to distal direction, as shown in FIGS. 9B-9C.

As shown in FIG. 9C, in a next step, a plurality of circumferential fibers 428 then may be arranged outside of the membrane 425 and the angled axial fiber bundles 427a-427d at locations distal to the proximal stent 460. The plurality of circumferential fibers 428 may be provided in accordance with the plurality of circumferential fibers 28, as shown in FIGS. 1-2. In a final step, one or more stents 438, such as zig-zag shaped stents provided as described above, may be arranged over the plurality of circumferential fibers 428 at locations distal to the proximal stent 460, as shown in FIG. 9C. The stent 438 may be secured to the membrane 425. The stent-graft 420 then may be prepared by mounting the membrane 425 on a lathe. The lathe may be rotated at a proper speed, such as 20 rpm, while applying a dilute polyurethane solution to cover all of the fibers disposed distal to the proximal stent 460. The stent-graft 420 then may be cured at about 65 degrees Celsius for about 2 hours while the lathe is rotated at the desired speed.

Advantageously, like the stent-grafts above, it is believed that the stent-graft 420 of FIGS. 9A-9C may provide a selectively reinforced membrane 425 that may better withstand physiological fluid flow in a proximal to distal direction. Further, by selectively orienting axial fibers 427, angled axial fiber bundles 427a-427d, and circumferential fibers 428 at predetermined locations along the length and circumference of the stent-graft 420, but not continuously along the stent-graft 420, a significantly reduced delivery profile may be achieved.

Figure 10:
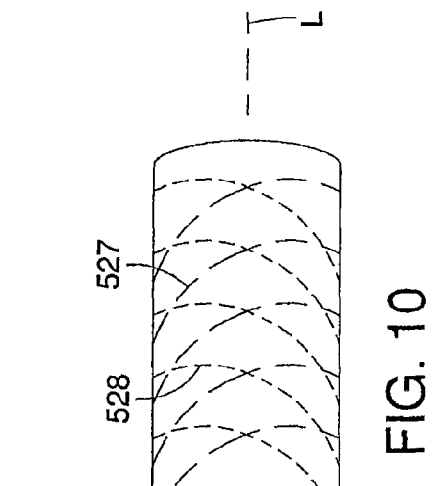
FIG. 10 is side view of a stent-graft according to a further alternative embodiment.

Referring to FIG. 10, in lieu of the generally axial and circumferential fibers 27 and 28 shown above, a further alternative stent-graft 520 may comprise a plurality of first fibers 527 and a plurality of second fibers 528, neither of which are substantially parallel or perpendicular to the longitudinal axis L of the prosthesis. The plurality of first fibers 527 and the plurality of second fibers 528 may be overlapping, but not interwoven. Such angled first and second fibers 527 and 528 may be more compliant than the axial and circumferential fibers 27 and 28 shown above, but still may be selectively arranged in a manner that may beneficially handle physiological loads, facilitate stent attachment to the membrane 525, and reduce the overall profile of the stent-graft 520, in the manner described above.

Referring now to FIGS. 11-21, alternative embodiments are described that eliminate the need to couple the stents to the membrane. In the embodiments of FIGS. 11-21, at least one surface enhancement member is secured to at least one stent. The surface enhancement member has stronger bonding properties with the membrane, relative to bonding properties of bare surfaces of the stent with the membrane.

Figure 11:
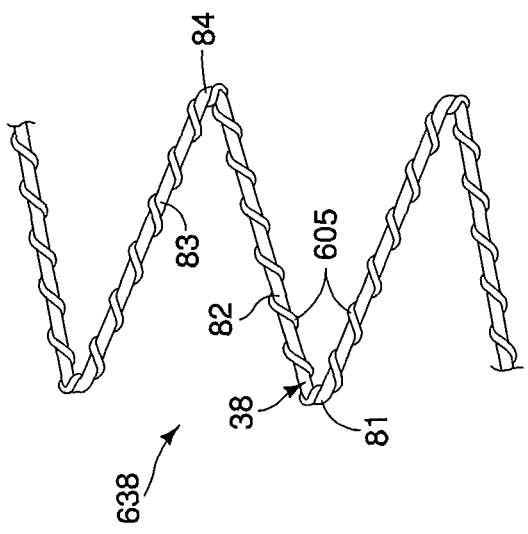
FIG. 11 is a side view of a portion of a stent and at least one surface enhancement member.

In the embodiment of FIG. 11, at least one surface enhancement member 605 is secured to at least a portion of the exemplary stent 38 of FIG. 2 to form an at least partially wrapped stent 638. While a Z-stent 38 is shown in FIG. 2, in the embodiment of FIG. 11 the stent may alternatively comprise a circular ring, one or more coils, a diamond-shape, or other suitable stent shapes.

In this example, one surface enhancement member 605 is continuously wrapped around the struts of the stent 38, including the substantially straight first segments 82 and second segments 83, as well as the bent segments in the form of proximal apices 81 and distal apices 84. Upon being wrapped around the struts of the stent 38, the surface enhancement member 605 may be held in place by, for example, knotting, adhesive or other mechanism, such as a cannula.

Optionally, multiple surface enhancement members 605 may be at least partially wrapped around the struts of the stent 38. If multiple surface enhancement members 605 are used, they may be coupled to one another, e.g., knotted together. Alternatively, each individual surface enhancement member 605 may span a predetermined distance along one or more strut segments. In an example of the latter embodiment, a first surface enhancement member 605 may span only along a length of one first segment 82 of the stent 38, while a second surface enhancement member 605 may span only along a length of one second segment 83 of the stent 38. In this example, the surface enhancement members 605 need not be wrapped around the proximal and distal apices 81 and 84, which may help reduce the delivery profile.

On the other hand, if one single surface enhancement member 605 is wrapped around an entire length of the stent 38, including all of the first and second segments 82 and 83, and the proximal and distal apices 81 and 84, as shown in FIG. 11, manufacturing become easier because the single surface enhancement member 605 can be wrapped around all of the segments relatively fast and then only one knotting or other securement step needs to be performed. Regardless of whether one or more surface enhancement members 605 are used, each surface enhancement member preferably is secured in a relatively taut manner to the struts of the stent 38, as depicted in FIG. 11.

The one or more surface enhancement members 605 may comprise various types of material that have stronger bonding properties with the membrane, relative to bonding properties of bare surfaces of the stent 38 with the membrane, as explained in detail in FIGS. 20-21 below. As one example, the one or more surface enhancement members 605 may comprise a filament, where the filament may comprise a suture material, yarn, a single-stranded material, a multiple-stranded material, thin wire having properties for enhanced bonding, and the like. The surface enhancement members 605 may achieve a relatively strong bond with the membrane, particularly when the membrane comprises a cured polymer. In particular, the one or more surface enhancement members 605 may comprise synthetic sutures that may be made from polypropylene, nylon, polyamide, polyethylene, and polyesters such as polyethylene terephthalate. These materials may be used as monosurface enhancement member suture strands, or as multisurface enhancement member strands in a braided, twisted or other multisurface enhancement member construction. While sutures are one example of surface enhancement members 605, other materials may be securely coupled to the stent that achieve a relatively strong bond with the membrane, as compared to the bond between bare surfaces of the stent and the membrane. In one exemplary embodiment, the properties of the filament may range from about 10 Denier to about 200 Denier.

The pitch of the one or more surface enhancement members 605 may be varied. In the example of FIG. 11, the pitch of a single surface enhancement member 605 is substantially constant in that adjacent helical loops are spaced apart about the same distance from one another, with about 6 helical loops per first segment 82, about 6 helical loops per second segment 83, and one helical loop disposed in the vicinity or under each of the proximal and distal apices 81 and 84. However, the winding pitch may be greater or lesser than depicted in FIG. 11, and may vary from one individual segment to the next, as described further in FIGS. 15-17 below.

Figure 12:
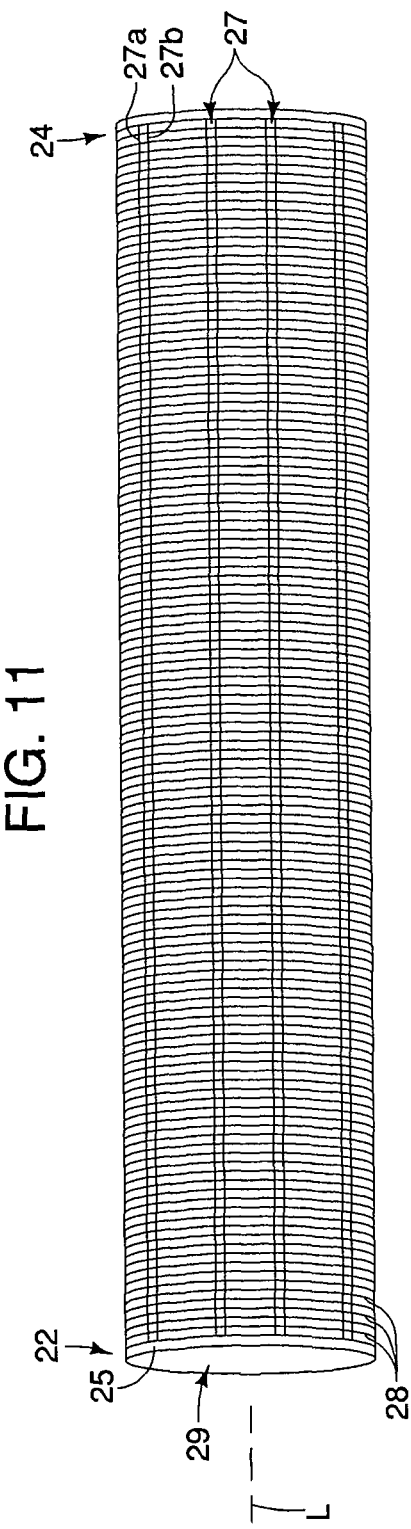
FIGS. 12-14 are side views illustrating exemplary method steps for manufacturing an endoluminal prosthesis including the stent and the at least one surface enhancement member of FIG. 11.
Figure 13:
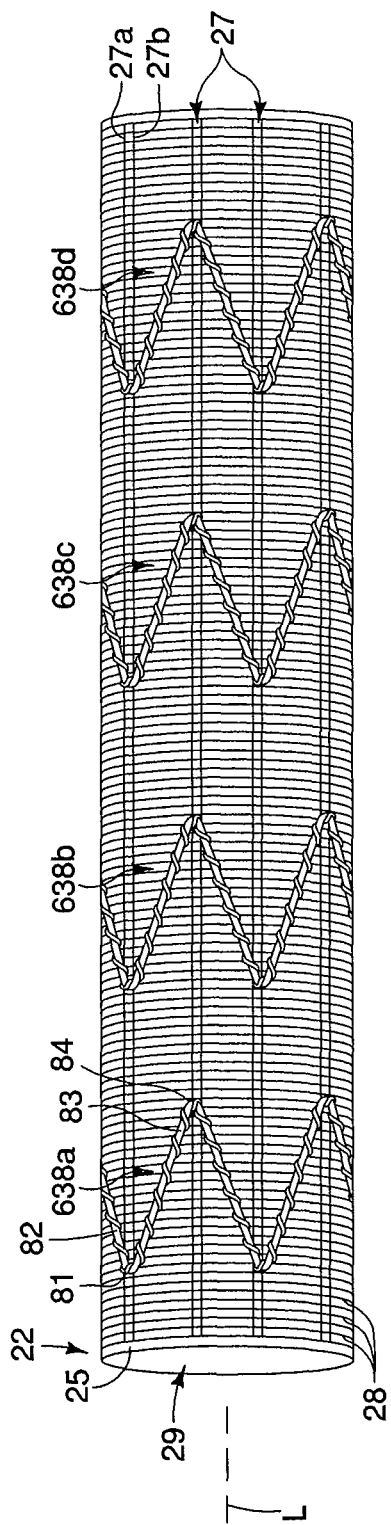
Figure 14:
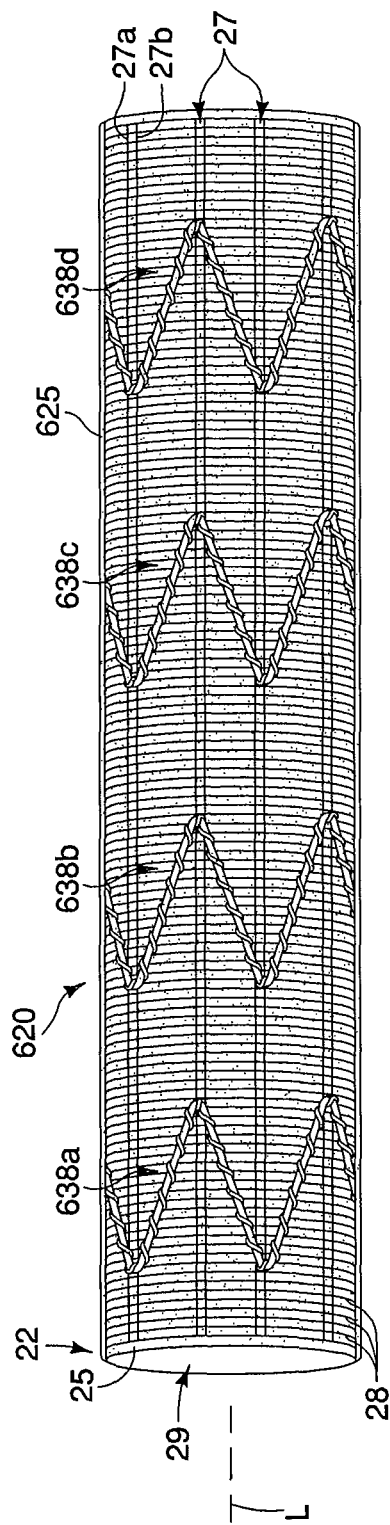

Referring to FIGS. 12-14, exemplary manufacturing steps to form a prosthesis including the wrapped stent 638 are described, which eliminate the need for conventional sutures. In a first step, any combination of the membrane 25, the axial fibers 27, the circumferential fibers 28 and/or the angled fibers 127, described in detail in various embodiments above, may be disposed around a mandrel into a desired form. In the example of FIG. 12, the membrane 25 is disposed internal to the axial fibers 27 and the circumferential fibers 28, while the angled fibers 127 are omitted. In this instance, the membrane 25 may be formed upon a mandrel, with the desired circumferential and axial fiber pattern being deposited externally thereof. Since suture attachment points are omitted in the embodiment of FIGS. 12-14, the bundled regions of FIGS. 1-2 may be omitted such that the circumferential fibers 28 are spaced apart about the same distance relative to each other. Optionally, however, the circumferential fibers 28 in the embodiment of FIGS. 12-14 may comprise a variable spacing relative to one another, e.g., circumferential fibers 28 may be bundled in areas where higher physiological loads are expected.

Referring to FIG. 13, in a next step at least one of the wrapped stents 638 is disposed over the membrane 25, the axial fibers 27 and the circumferential fibers 28. In this example, four wrapped stents 638a, 638b, 638c and 638d are positioned at approximately equal intervals along the axial length of the prosthesis. In FIG. 14, the membrane 25, the axial fibers 27, the circumferential fibers 28 and the wrapped stents 638a-638d are then coated with a membrane 625, which may comprise a polymeric solution such as Thoralon®, as described above relative to the membrane 25. The completed stent-graft 620 then may be cured or dried at about 65 degrees Celsius for about 2 hours while the lathe is rotated at the desired speed.

Advantageously, the completed stent-graft 620 of FIG. 14, including the wrapped stents 638a-638d, comprises an enhanced structural integrity without the need to couple the individual stents to the membrane 25 and/or the membrane 625 using time-consuming suturing techniques. The test data discussed in FIGS. 20-21 below supports the conclusion that stent-grafts employing the stents 38 having one or more surface enhancement members 605 disclosed herein yield a more durable bond between the components, relative to stent-grafts that utilize bare stents 38 lacking a surface enhancement member 605. In particular, the inventor has determined that by securing the at least one surface enhancement member 605 to the stents 38 prior to application and curing of the membranes 25 and 625, the cured membranes better adhere to the surfaces of the one or more surface enhancement members 605 secured to the stents, as opposed to the bare metal surfaces of the stents.

One or both membranes 25 and 625 may be used in the embodiment of FIGS. 12-14. If both membranes 25 are used, as shown in FIGS. 12-14, the membrane 25 forms an inner membrane, while the membrane 625 forms an outer membrane. In such an embodiment, the axial fibers 27, the circumferential fibers 28, and the stents 638a-638d having the surface enhancement members 605 are generally sandwiched between the inner membrane 25 and the outer membrane 625. The cured inner and outer membranes 25 and 625 may be securely bonded to the axial fibers 27, the circumferential fibers 28, and the surface enhancement members 605 secured to the stents 38.

In alternative embodiments, the inner membrane 25 may be omitted. In the latter example, the axial fibers 27, the circumferential fibers 28 and/or the angled fibers 127 are arranged directly over a mandrel without a membrane thereon, the wrapped stents 638a-638d are then arranged over the fibers, and the membrane 625 is applied over the wrapped stents 638a-638d and the fibers. The membrane 625 still becomes securely coupled to the one or more surface enhancement members 605 secured to the stents 38, as well as being bonded to the various axial fibers 27 and circumferential fibers 28, without the need to fully encapsulate the stents 38 and the various fibers between separate inner and outer membranes.

Alternatively, only an inner membrane 25 may be employed, and the outer membrane 625 may be omitted. In this instance, the stent-graft may be cured in the configuration shown in FIG. 13. Upon curing, the inner membrane 25 becomes securely bonded to the one or more surface enhancement members 605 that are secured to the stents 38, as well as being bonded to the various axial fibers 27 and circumferential fibers 28, without the need to fully encapsulate the stents 38 and the various fibers between separate inner and outer membranes.

Referring to FIGS. 15-17, as noted above the pitch of the one or more surface enhancement members 605 may be varied as part of alternative wrapped stents 638', 638" and 638'". For illustrative clarity, the three-dimensional nature of the surface enhancement members 605 being wrapped around the stent struts is omitted in FIGS. 15-17. In the example of FIG. 15, the pitch of one or more surface enhancement members 605' is substantially constant as adjacent helical loops are spaced apart about the same distance from one another, but a reduced pitch is provided, relative to the embodiment of FIG. 11, with about 3 helical loops per first segment 82 and about 3 helical loops per second segment 83. In the example of FIG. 16, the pitch of one or more surface enhancement members 605" is substantially constant, but a higher pitch is provided, relative to the embodiment of FIG. 11, with about 8 helical loops per first segment 82 and about 8 helical loops per second segment 83. In the example of FIG. 17, the pitch of one or more surface enhancement members 605'" is varied along the stent with about 3 helical loops along one of the first and second segments 82 and 83, about 4 helical loops along the adjacent first and second segments 82 and 83, about 8 helical loops along the next adjacent first and second segments 82 and 83, and about 13 helical loops along the next adjacent first and second segments 82 and 83.

Various advantages are achieved in the embodiments of FIGS. 15-17. By providing a reduced pitch as shown in FIG. 15, a lower profile may be achieved while still promoting an enhanced durable bond between the surface enhancement members 605' and the membranes 25 and/or 625, without the need for suturing the stent to the one or more membranes. By providing a higher pitch as shown in FIG. 16, the surface area presence of the one or more surface enhancement members 605" is increased, allowing the cured membranes 25 and/or 625 to better adhere to the surfaces of the surface enhancement member 605 secured to the stent. Additionally, the embodiment of FIG. 16 reduces the area of exposed metal surfaces of the stents, which the cured membrane may be less likely to bond to, relative to the surface enhancement members 605". In the embodiment of FIG. 17, the variable pitch yields advantages of both a reduced profile in areas of lower pitch and stronger bonding to the membranes 25 and/or 625 in areas of higher pitch. As will be apparent, the wrapping patterns shown in FIGS. 11 and 15-17 are not the only patterns that may be provided. Other patterns may be provided in accordance with the principles herein.

Figure 18:
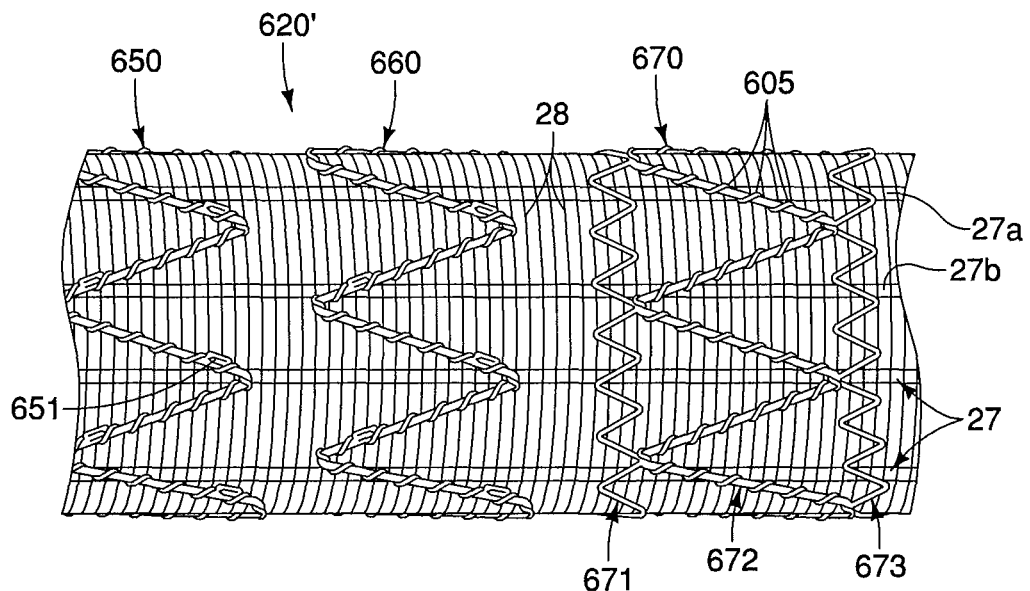
FIG. 18 is a side view of a portion of an endoluminal prosthesis including a plurality of stents having at least one surface enhancement member.

Additionally, other stent structures may be provided than shown in FIGS. 11 and 13-17. Referring to FIG. 18, in an alternative embodiment, stent-graft 620' is manufactured according to the same techniques used for the stent-graft 620 of FIGS. 12-14, but a plurality of alternative stents 650, 660 and 670 are provided. The stents 650 and 660 each comprise a zig-zag shape similar to the stent 638 above, but comprise a plurality of integral barbs 651 formed therein. The stent 670 comprises three sections 671, 672 and 673, with the first and third sections 671 and 673 comprising a relatively short axial length and high number of apices, and the intermediate second section 672 comprising a longer axial length and fewer apices, as shown in FIG. 18. One or more surface enhancement members 605 are secured to each of the stents 650, 660 and 670, as discussed in FIG. 11 above. When assembly of the stent-graft 620' of FIG. 18 is completed according to the techniques of FIGS. 12-14 described above, the surface area presence of the one or more surface enhancement members 605 secured to the stents 650, 660 and 670 yields a stronger bond with the membranes 25 and/or 625. While zig-zag shaped stents are generally depicted herein, the at least one surface enhancement member 605 may be secured to stents having any suitable shape, including but not limited to stents having struts that are hoop-shaped, diamond-shaped, and the like.

Figure 19:
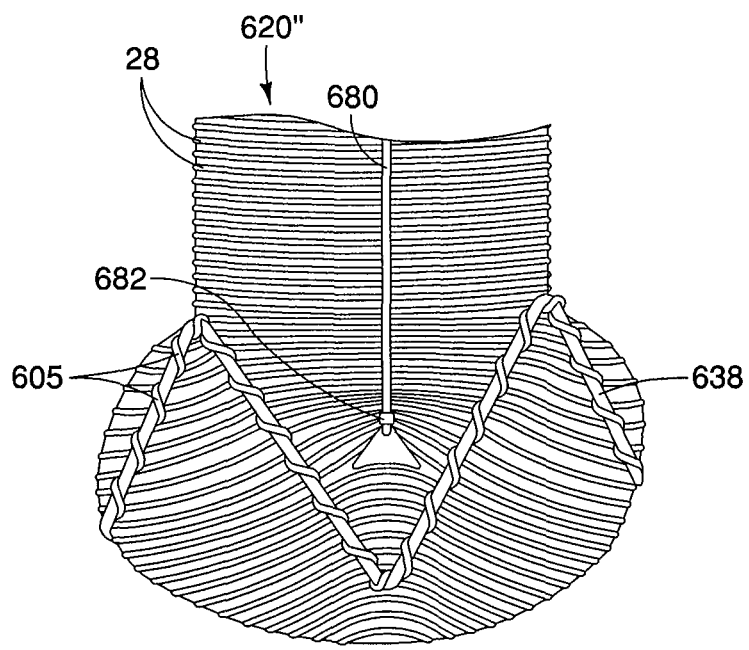
FIG. 19 is a side view illustrating a load testing arrangement for an endoluminal prosthesis including a stent and at least one surface enhancement member.
Figure 20:
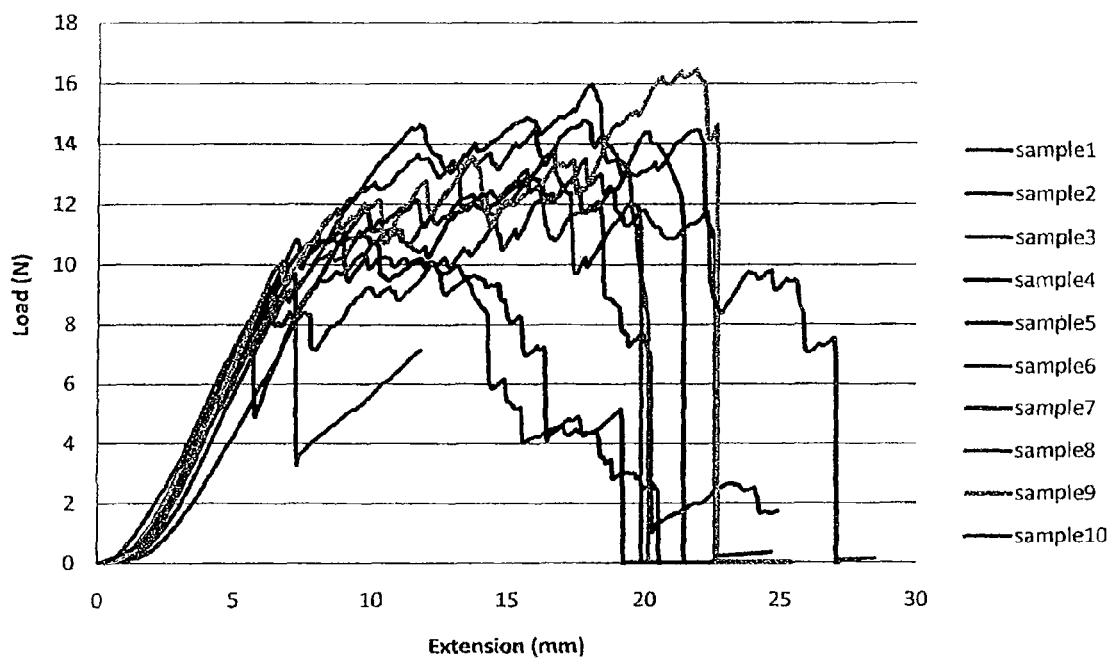
FIGS. 20-21 are, respectively, charts illustrating tensile test data for sample endoluminal prostheses including a stent with at least one surface enhancement member present, and with a surface enhancement member omitted.
Figure 21:
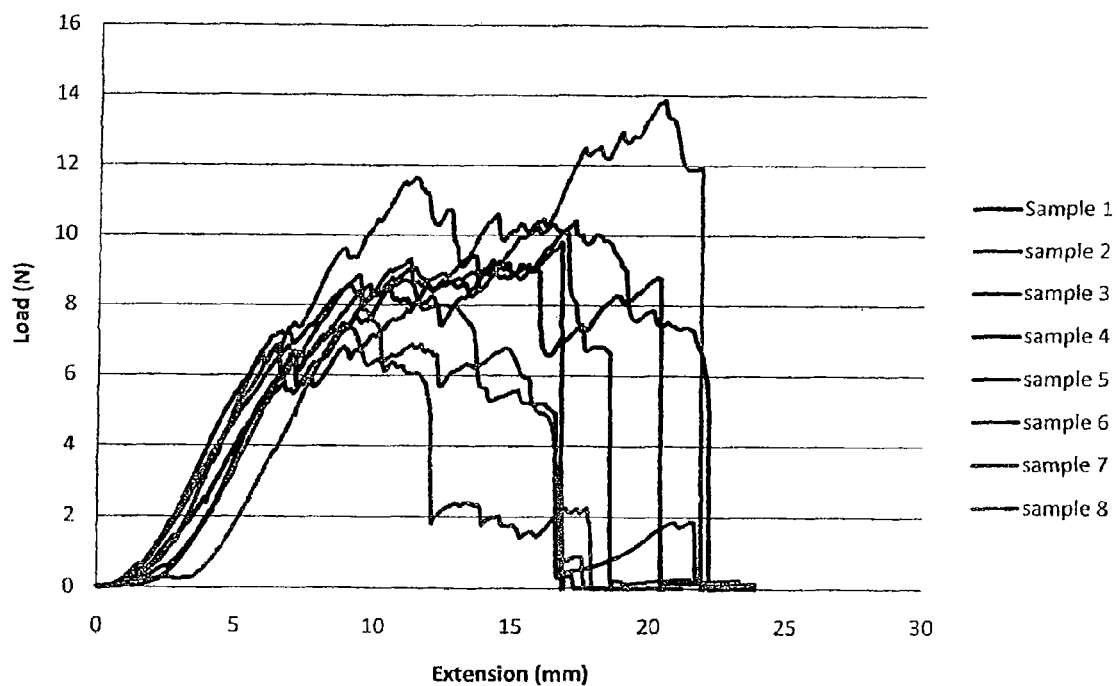

Referring now to FIGS. 19-21, load testing results performed by the inventor indicate that a stent having one or more surface enhancement members 605 secured thereto provides stronger bonding characteristics as part of a cured polymer stent-graft. In the test shown in FIG. 19, a sample stent-graft 620" is formed generally in accordance with the stent-graft 620 of FIG. 14, with the exception that axial fibers 27a and 27b are omitted. The stent-graft 620" comprises the wrapped stent 638 of FIG. 11, which has one or more surface enhancement members 605 secured to the stent 38. In this particular test, polyester filaments were used as the surface enhancement members 605. A load testing element 680 is coupled to a portion of the stent-graft 620" and then is retracted proximally, while the distal end of the stent-graft 620" is affixed to a secure, non-movable member. The maximum load to failure was determined as the amount of force required to rupture a portion of the stent-graft 620" during retraction of the load testing element 680. The inventor tested multiple different stent-grafts 620", which were formed with at least one surface enhancement member 605 secured to the stent 38. The results of 10 samples are shown in FIG. 20.

The inventor additionally tested ten stent-graft samples that omitted the surface enhancement members 605 secured to the stent 38, but were otherwise manufactured in accordance with the stent-graft 620 of FIG. 14, with the exception that axial fibers 27a and 27b were omitted. The results of 10 samples that omitted the surface enhancement members 605 are shown in FIG. 21.

Table 1 presents relevant data associated with the testing performed in FIGS. 20-21.

TABLE 1

Tabulated Data from Stent-Graft Tensile Testing

|  | Stent-Grafts Provided With At Least One Surface Enhancement Member Secured to Stent | Stent-Grafts Provided Without At Least One Surface Enhancement Member Secured to Stent |
| --- | --- | --- |
| Average Max. Load (N) | 13.44 | 9.78 |
| Average Extension at Max. Load (mm) | 15.05 | 14.31 |
| Min. (N) | 9.69 | 7.47 |
| Max. (N) | 16.47 | 13.86 |

On average, the stent-grafts provided with at least one surface enhancement member 605 secured to the stent 38 yielded a 37.4% higher tensile strength than the samples that omitted the surface enhancement member 605. This percentage is calculated as 13.44 N minus 9.78 N=3.66 N difference between the sample categories; and 3.66 N divided by 9.78 N is 37.4%. Additionally, the stent-grafts provided with at least one surface enhancement member 605 secured to the stent 38 yielded a 5% higher average extension at maximum load relative to the samples that omitted the surface enhancement member. Further, the stent-grafts provided with at least one surface enhancement member 605 secured to the stent 38 performed better at the individual minimum load (9.69 N) and individual maximum load (16.47 N) relative to the samples that omitted the surface enhancement member.

In sum, the test data shows that stent-grafts provided with at least one surface enhancement member secured to the stent, in accordance with the principles disclosed herein, provides a more durable bond between the prosthesis components. In particular, the at least one surface enhancement member 605 has stronger bonding properties with the membrane, relative to bonding properties of bare surfaces of the stent with the membrane.

While various embodiments of the invention have been described, it will be apparent to those of ordinary skill in the art that many more embodiments and implementations are possible within the scope of the invention. Accordingly, the invention is not to be restricted except in light of the attached claims and their equivalents. Moreover, the advantages described herein are not necessarily the only advantages of the invention and it is not necessarily expected that every embodiment of the invention will achieve all of the advantages described.

I claim:

1. An endoluminal prosthesis, comprising:
    at least one stent having a surface;
    at least one surface enhancement member, separate from the stent, wrapped around at least one portion of the surface of the stent, wherein the at least one surface enhancement member is arranged in a plurality of helically wrapped turns around a perimeter of an individual stent strut;
    a first membrane having a lumen for allowing fluid flow therethrough, the first membrane disposed coaxially about the at least one stent and the at least one surface enhancement member, and bonded to the at least one surface enhancement member,
    where the at least one surface enhancement member is helically wrapped around the perimeter of the individual stent strut without being woven into the first membrane, and
    where the bond between the first membrane and the at least one surface enhancement member has a bond strength greater than a bond strength between the first membrane and the surface of the stent.

2. The endoluminal prosthesis of claim 1, where the surface enhancement member is secured to the stent prior to a coaxial overlapping state of the stent and the first membrane.

3. The endoluminal prosthesis of claim 1, where the surface enhancement member comprises a filament.

4. The endoluminal prosthesis of claim 1 where the first membrane comprises a cured polymer solution.

5. The endoluminal prosthesis of claim 4, where the polymer encapsulates the stent.

6. The endoluminal prosthesis of claim 1 further comprising a second membrane, where the first membrane is disposed internal to the stent, and the second membrane is disposed external to the stent.

7. The endoluminal prosthesis of claim 1 where the at least one surface enhancement member is continuously wrapped around a length of the stent and knotted upon itself.

8. The endoluminal prosthesis of claim 1 where the stent comprises a zig-zag shape having a plurality of generally straight segments separated by proximal and distal apices, where the at least one surface enhancement member is wrapped around at least a portion of each of the generally straight segments and the proximal and distal apices.

9. The endoluminal prosthesis of claim 1 further comprising a plurality of circumferential fibers arranged in a desired orientation relative to the first membrane, where a plurality of the circumferential fibers are spaced apart relative to one another, and where the first membrane bonds with the at least one surface enhancement member and the plurality of circumferential fibers.

10. An endoluminal prosthesis, comprising:
    at least one stent comprising at least one strut, the strut having a circumferential surface;
    at least one filament separate from the strut, wrapped around at least a portion of the strut, wherein the at least one filament is arranged in a plurality of helically wrapped turns around a perimeter of an individual stent strut;
    a first membrane having a lumen for allowing fluid flow therethrough, the first membrane disposed coaxially about the at least one stent and the at least one filament, and bonded to the at least one filament,
    where the at least one filament is helically wrapped around the perimeter of the individual stent strut without being woven into the first membrane, and
    where the bond between the first membrane and the at least one filament has a bond strength greater than a bond strength between the first membrane and an exposed surface of the stent.

11. The endoluminal prosthesis of claim 10 where the stent comprises a zig-zag shape having a plurality of generally straight segments separated by proximal and distal apices, where the at least one filament is wrapped around at least a portion of each of the generally straight segments and the proximal and distal apices.

12. The endoluminal prosthesis of claim 10 where the first membrane comprises a cured polymer solution.

13. The endoluminal prosthesis of claim 10 further comprising a second membrane, where the first membrane is disposed internal to the stent, and the second membrane is disposed external to the stent.

14. An endoluminal prosthesis, comprising:
    a first membrane comprising a polymer solution and having a lumen for allowing fluid flow;
    a stent having contracted and expanded states; and
    at least one surface enhancement member, separate from the stent, which is secured to the stent prior to coaxial overlapping of the stent and the first membrane, wherein the at least one surface enhancement member is arranged in a plurality of helically wrapped turns around a perimeter of an individual stent strut;
    wherein the at least one surface enhancement member is helically wrapped around the perimeter of the individual stent strut without being woven into the first membrane, and
    wherein, after coaxial overlapping of the stent and the first membrane, curing of the polymer solution causes surfaces of the at least one surface enhancement member to securely bond with the polymer solution.

15. The endoluminal prosthesis of claim 14 further comprising a second membrane comprising a polymer solution, where the first membrane is disposed internal to the stent and the second membrane is disposed external to the stent.

16. The endoluminal prosthesis of claim 14 where the at least one surface enhancement member comprises a suture that is wrapped around a perimeter of at least one segment of the stent.

17. The endoluminal prosthesis of claim 14 where the at least one surface enhancement member is continuously wrapped around a length of the stent and knotted upon itself.

* * * * *